United States Patent
Ikhlef et al.

(10) Patent No.: US 8,761,333 B2
(45) Date of Patent: Jun. 24, 2014

(54) LOW RESOLUTION SCINTILLATING ARRAY FOR CT IMAGING AND METHOD OF IMPLEMENTING SAME

(75) Inventors: Abdelaziz Ikhlef, Hartland, WI (US); David Michael Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 392 days.

(21) Appl. No.: 13/208,445

(22) Filed: Aug. 12, 2011

(65) Prior Publication Data

US 2013/0039458 A1 Feb. 14, 2013

(51) Int. Cl.
*A61B 6/03* (2006.01)
*B23P 11/00* (2006.01)
*G06K 9/36* (2006.01)

(52) U.S. Cl.
USPC ............... 378/19; 378/154; 382/284; 29/428

(58) Field of Classification Search
CPC ..................................... A61B 6/4266
USPC ..................... 378/154; 250/370.11
See application file for complete search history.

(56) References Cited

U.S. PATENT DOCUMENTS

| | | | |
|---|---|---|---|
| 6,259,098 B1 | 7/2001 | Vafi et al. | |
| 6,389,096 B1 | 5/2002 | Hoffman et al. | |
| 6,740,883 B1 | 5/2004 | Stodilka et al. | |
| 7,016,455 B2 | 3/2006 | Bruder et al. | |
| 7,127,096 B2 | 10/2006 | Kaufman et al. | |
| 7,149,331 B1 | 12/2006 | Kaufman et al. | |
| 7,409,035 B2 | 8/2008 | Kaufman et al. | |
| 7,522,744 B2 | 4/2009 | Bai et al. | |
| 7,564,940 B2 | 7/2009 | Mattson et al. | |
| 7,746,974 B2 | 6/2010 | Shukla | |
| 7,782,999 B2 | 8/2010 | Lewalter et al. | |
| 7,787,112 B2 | 8/2010 | Rahn et al. | |
| 7,888,647 B2 | 2/2011 | Warner et al. | |
| 7,894,576 B2 | 2/2011 | Carmi | |
| 7,933,010 B2 | 4/2011 | Rahn et al. | |
| 2008/0095314 A1* | 4/2008 | Katcha et al. | 378/101 |
| 2009/0148023 A1* | 6/2009 | Spahn | 382/132 |

* cited by examiner

*Primary Examiner* — Hoon Song
*Assistant Examiner* — Danielle Fox
(74) *Attorney, Agent, or Firm* — Ziolkowski Patent Solutions Group, SC (57) ABSTRACT

A CT system includes a rotatable gantry having an opening to receive an object to be scanned, an x-ray source configured to project an x-ray beam toward the object, and a detector array configured to detect x-rays passing through the object. The detector array includes a first array of pixels positioned to receive x-rays that pass to the detector array outside a first field-of-view (FOV) to a second FOV, the first array of pixels providing a first resolution, and a second array of pixels positioned to receive x-rays passing through the first FOV, the second array of pixels providing a second resolution that is different from the first resolution. The system includes a data acquisition system (DAS) configured to receive outputs from the detector array, and a computer programmed to acquire projections of imaging data of the object, and generate an image of the object using the imaging data.

14 Claims, 7 Drawing Sheets

LOW RESOLUTION SCINTILLATING ARRAY FOR CT IMAGING AND METHOD OF IMPLEMENTING SAME

BACKGROUND OF THE INVENTION

Embodiments of the invention relate generally to diagnostic imaging and, more particularly, to a method and apparatus using low resolution imaging arrays in an imaging application.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotating about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

With recent advances in CT clinical applications, it is desirable to cover an entire organ in a single gantry rotation and in a single projection, so that an entire cardiac acquisition can be completed in a single cardiac cycle. A heart can typically be covered in a cylindrical shaped region with a diameter of 25 cm (in an x-y plane) and a length of 12 cm (in a slice or z-direction) for most patients. In neural perfusion studies it is desirable to cover at least 12 cm along the patient long axis (in z-direction) while continuously scanning the patient during contrast uptake and washout. There are CT scanners on the market that cover, for example, 16 cm along the z-axis and 50 cm field-of-view (FOV) across the patient (in an x-y plane), which are well in excess of that necessary to provide imaging information for cardiac and neural perfusion studies. Thus, for cardiac and neural perfusion studies the region-of-interest (ROI) in the x-y plane is significantly smaller than the full detector coverage of 50 cm.

Scanning a typical organ (i.e., heart or brain) with a 50 cm FOV often provides little additional relevant imaging information, thus a 35 cm FOV is typically adequate for many organ imaging applications. Thus, from a design and cost point of view, it is desirable to reduce the coverage to a FOV (in x-y plane) that is slightly larger than the object-of-interests that are being imaged. For CT reconstruction, however, information outside the ROI may be necessary to faithfully reconstruct an object-of-interest within even a limited FOV. Without this information, typical truncation artifacts may result.

Although recent attempts have been made to reconstruct images based on truncated projections, these reconstruction techniques typically result in unstable solutions or require specific knowledge inside the reconstruction FOV. When imaging an object or patient in a larger FOV, relevant imaging information may be, in fact, provided over the entire FOV (50 cm in the above example). Thus, some imaging applications provide adequate imaging data over a 35 cm FOV by using limited additional information outside the FOV to avoid truncation errors, while other imaging applications benefit from obtaining relevant imaging data over the entire 50 cm FOV. In both cases (limited FOV and full FOV), it is desirable to obtain imaging data using a detector having a full 50 cm FOV. The cost of such a scanner can be prohibitive, however.

Therefore, it would be desirable to design an apparatus and method to reduce cost of a CT system, while providing full and limited FOV imaging capability.

BRIEF DESCRIPTION OF THE INVENTION

The invention is a directed method and apparatus for imaging using a low resolution scintillating array.

According to one aspect, a CT system includes a rotatable gantry having an opening to receive an object to be scanned, an x-ray source configured to project an x-ray beam toward the object, and a detector array configured to detect x-rays passing through the object. The detector array includes a first array of pixels positioned to receive x-rays that pass to the detector array outside a first field-of-view (FOV) to a second FOV, the first array of pixels providing a first resolution, and a second array of pixels positioned to receive x-rays passing through the first FOV, the second array of pixels providing a second resolution that is different from the first resolution. The system includes a data acquisition system (DAS) configured to receive outputs from the detector array, and a computer programmed to acquire projections of imaging data of the object, and generate an image of the object using the imaging data.

According to another aspect, a method of fabricating a detector assembly includes positioning a first detector array, having detector modules comprising a first resolution, to receive imaging data over a second field-of-view (FOV) and outside a first FOV, and positioning a second detector array, having detector modules comprising a second resolution, to receive imaging data over the first FOV, wherein the second resolution is different from the first resolution.

According to yet another aspect, a non-transitory computer readable storage medium having stored thereon a computer program comprising instruction which, when executed by a computer, cause the computer to obtain first imaging data from a first plurality of detector modules, having a first resolution, that are positioned to receive the first imaging data over a second field-of-view (FOV) that is outside of a first FOV, obtain second imaging data from a second plurality of detector modules, having a second resolution, that are positioned to receive the second imaging data over the first FOV, wherein the second resolution is greater than the first resolution, and reconstruct an image using the imaging data.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
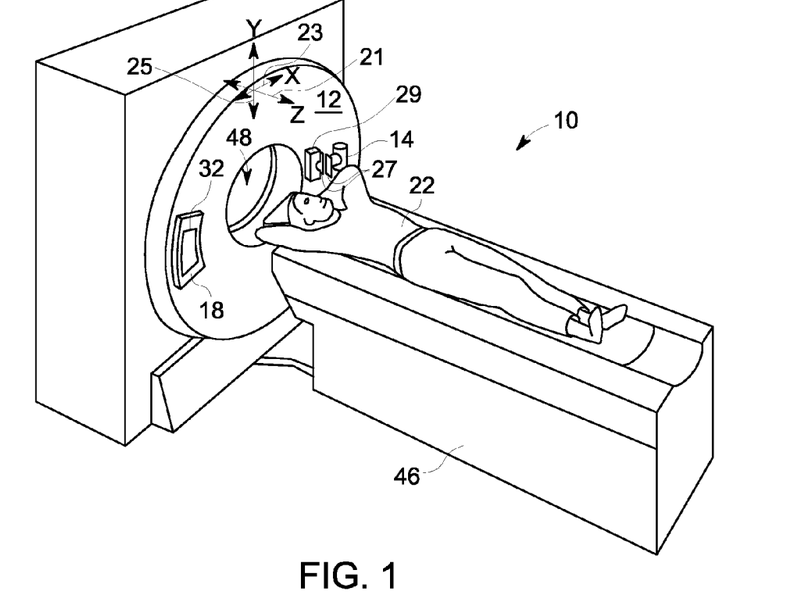
FIG. 1 is a pictorial view of a CT imaging system.
Figure 2:
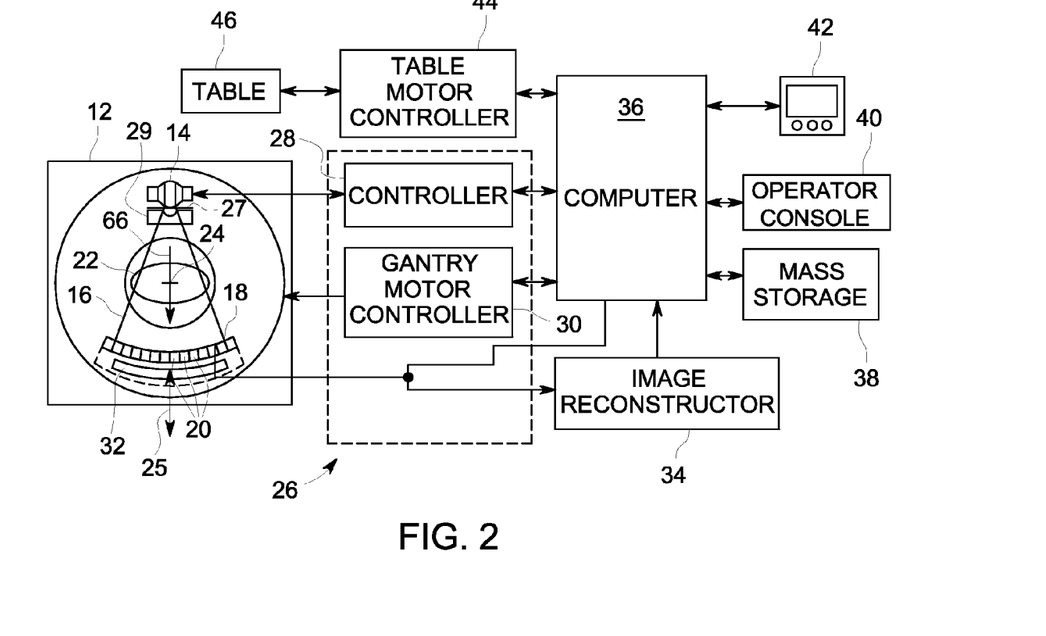
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. Imaging system 10 includes a pre-patient collimator 27 and a bowtie filter 29. Pre-patient collimator 27 is configured to control a beam width, in a z-direction and as known in the art, between x-ray source 14 and detector assembly 18. Detector assembly 18 is formed by a plurality of detectors 20 and data acquisition systems (DAS) 32. The plurality of detectors 20 sense the projected x-rays 16 that pass through medical patient 22. DAS 32 converts the data from detectors 20 to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes a controller 28 that provides power and timing signals to an x-ray source 14 as well as motion control for operation of pre-patient collimator 27 and bowtie filter 29, and control mechanism 26 includes a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

As commonly understood in the art, patient 22 is generally translated along a z-direction 21, commonly referred to as a slice-direction, of gantry 12. As also commonly understood in the art, detector assembly 18 is caused to rotate circumferentially in an x-direction 23, or channel direction, of gantry 12. Thus, x-rays 16 travel generally in a y-direction 25 and through detector assembly 18 as they emit from x-ray source 14 and pass through patient 22.

Figure 3:
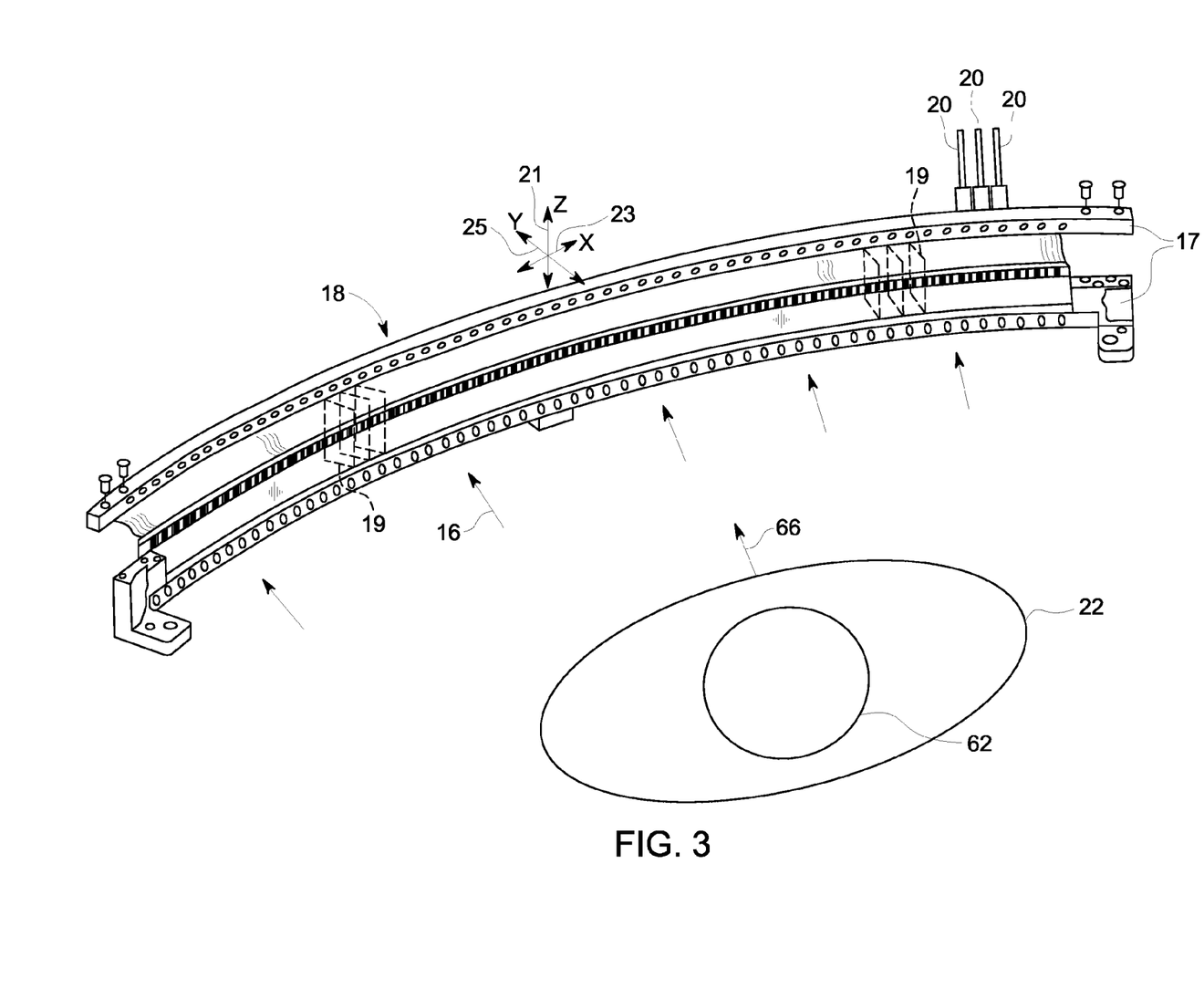
FIG. 3 is a perspective view of one embodiment of a CT system detector array.

As shown in FIG. 3, detector assembly 18 includes rails 17. Commonly, detector assembly 18 may include collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20 along x-direction 23, for an array size of 64×16 of pixel elements 50 (for a 64 slice detector 20). As a result, detector assembly 18 includes 912 columns (16× 57 detectors) which allows numerous simultaneous slices of data to be collected with each rotation of gantry 12. Thus, consistent with FIGS. 1 and 2, z-direction 21 (or slice direction), x-direction 23 (or channel direction), and y-direction 25 are illustrated. In one example, two detectors 18 are positioned along z-direction 21, enabling in this example 2×64=128 slices of z-coverage in detector assembly 18. In another example, eight detectors 18 are positioned along z-direction 21, enabling in this example 8×64=512 slices of z-coverage in detector assembly 18. In fact, according to the invention, any number of detectors 20 may be positioned along z-direction 21, enabling numerous designs having numerous corresponding options for numbers of slices covered and varying amounts of z-coverage. It is to be understood that detector 20 is not limited to having 16 channels in x-direction 23 or 64 slices in z-direction 21, but that any numbers of slices and channels may be included in detector 20, according to the invention. For instance, each detector 20 may be comprised of 16 channels in x-direction 23 and 32 channels in z-direction 21.

Figure 4:
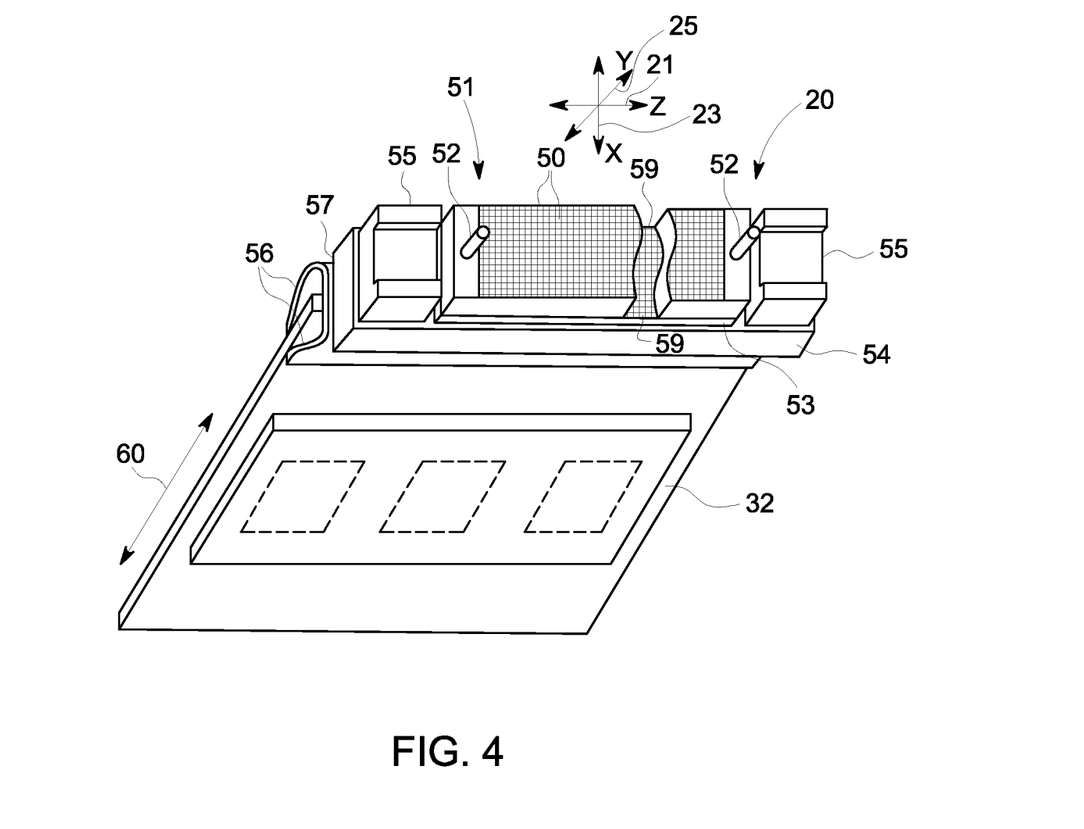
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal. Consistent with the earlier discussion, z-direction 21 defines also a slice direction and, as understood in the art, the number of detector elements 50 positioned along z-direction 21 and in detector 20 defines the number of imaging slices obtainable in an imaging system, such as imaging system 10 of FIGS. 1 and 2. Typically and as stated, the number of slices or detector elements 50 along z-direction 21 may be 16, 64, 256, or 512. However, it is contemplated that the invention is not to be so limited, and that any number of slices may be collimated along x-direction 23, according to the invention. X-direction 23, or channel direction, is also illustrated as it relates to detector 20. Typically, each detector 20 includes 16 detector elements 50 in x-direction 23, and there are typically 57 such detectors 20 positioned in detector assembly 18. However, it is contemplated that the invention is not to be so limited, and that any number of channels may be collimated, according to the invention. Y-direction 25 is illustrated, having a direction 60 that is generally parallel with DAS 32.

Referring back to FIG. 3, three exemplary detectors 20 (also referred to as detector modules) are illustrated therein (of the 57 modules described above, for example). During imaging of, for instance, patient 22 of FIGS. 1 and 2, a region-of-interest (ROI) 62 may be imaged by obtaining imaging data from the detectors 20, mounted on detector assembly 18. Thus, as gantry 12 is rotated, x-rays 16 emit from source 14, through patient 22, and are received by detectors 20. Typically, imaging data is obtained of ROI 62 as either a helical or an axial scan is performed, as known in the art. Commonly, a centermost channel, at the center of detector assembly 18 along x-direction 23, is defined as the isochannel or isocenter, which receives x-rays that pass along a centermost ray 66 to detector assembly 18. For further illustration, referring back to FIG. 2, ray 66 shows centermost ray 66 passing generally through center-of-rotation 24.

Figure 5:
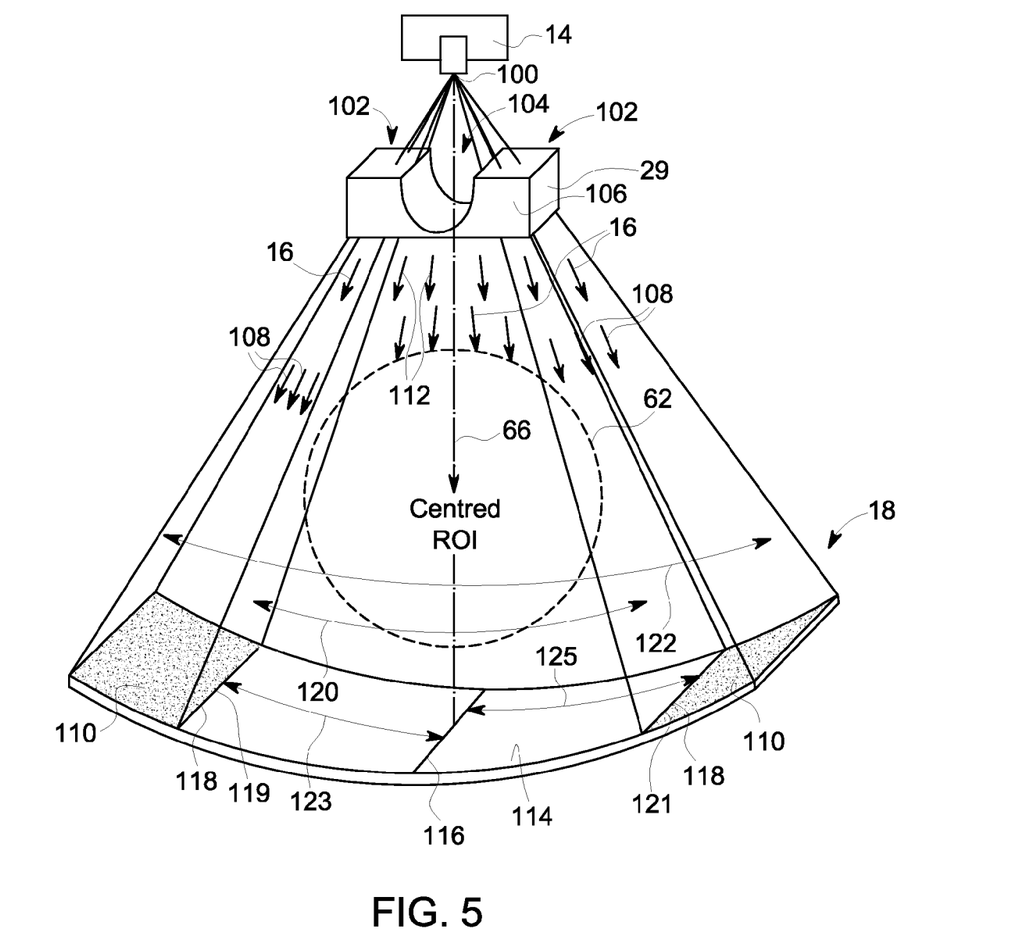
FIG. 5 is a perspective view of components of an imaging system for illustration of fields-of-view as they correspond to a detector array, according to an embodiment of the invention.

Referring to FIG. 5, system 10 includes a focal spot 100 of x-ray source 14, from which x-rays 16 emit toward detector array 18. Bowtie filter 29 includes a first x-ray filtration region 102 (two outermost regions of bowtie filter 29) and a second x-ray filtration region 104 (central region of bowtie filter 29), which are fabricated from an x-ray attenuation material 106. Bowtie filter 29 is positioned to attenuate x-rays 16 that pass from focal spot 100 to detector array 18. X-rays 108 that pass through first x-ray filtration region(s) 102 of bowtie filter 29 pass to first arrays of pixels 110 of detector array 18, and x-rays 112 that pass through second x-ray filtration region 104 of bowtie filter 29 pass to a second array of pixels 114 of detector array 18. X-rays 112 pass to second array of pixels 114, which includes an isochannel 116 that is a channel positioned to receive x-rays 16 that pass along centermost ray 66. As described, detector array 18 is electrically coupled to DAS 32, which is coupled to computer 36. Thus, computer 36 is programmed to acquire projections of image data from DAS 32, which is configured to acquire image data from detector array 18.

Second array of pixels 114 and first arrays of pixels 110 are separated by boundaries 118. First and second x-ray filtration regions 102, 104, along with corresponding first and second arrays of pixels 110, 114, are selected in order that a first field-of-view (FOV) 120 corresponds generally to ROI 62, and a second FOV 122, larger than first FOV 120, corresponds generally to first and second arrays of pixels 110, 114. That is, first arrays of pixels 110 are positioned to receive x-rays 108 that pass to detector array 18 extending outside first FOV 120 and through second FOV 122, and second array of pixels 114 is positioned to receive x-rays 108 passing through first FOV 120. Further, as stated, boundaries 118 separate second array of pixels 114 and first arrays of pixels 110. As shown, boundaries 118 include a first boundary 119 and a second boundary 121. First boundary 119 is positioned a first distance 123 from isochannel 116, and second boundary 121 is positioned a second distance 125 from isochannel 116. According to one embodiment, first and second distances 123, 125 are equal to one another, resulting in first arrays of pixels 110 being symmetrically positioned with respect to isochannel 116. However, according to another embodiment, first and second distances 123, 125 are different from one another, resulting in first arrays of pixels 110 being asymmetrically positioned with respect to isochannel 116. Further, as can be seen in FIG. 5, the asymmetric positions of boundaries 119, 121 are positioned as such and with respect to a plane of rotation of source 14 and detector assembly 18 as it is caused to rotate in system 10.

Figure 6:
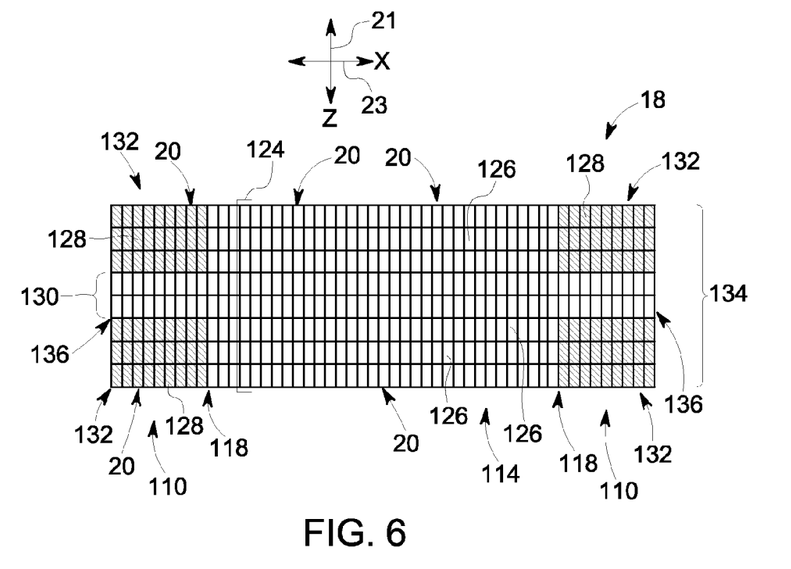
FIG. 6 is an illustration of a plan view of a detector array according to an embodiment of the invention.

According to the invention, detector array 18 may be configured to encompass a z-width that may include 16, 64, 256, or 512 slices, as examples. However, according to the invention, modules or detectors 20 may be positioned in detector array 18 having different levels of resolution. Referring now to FIG. 6, a plan view of detector array 18 is illustrated that includes a plurality of detector modules 20, according to the invention. Consistent with FIG. 5, detector array 18 includes modules 20 that include first arrays of pixels 110 and second array of pixels 114, each separated by boundaries 118. Second array of pixels 114, in this embodiment, includes modules having eight (8) blocks of packs along z-direction 21, each pack having 32 pixel slices therein. That is, although detector 20 of FIG. 4 was illustrated having a single pack 51 having 64 pixel slices, any number of packs may be used to obtain the desired number of pixels in z-direction 21, that may be separated by, for instance, alignment pins 52 (as illustrated with respect to detector 20 in FIG. 4). Thus, in the illustrated embodiment, eight packs 124 are shown, each having 32 pixel slices, for coverage of 256 slices. In one embodiment, 32 slices of coverage along z-direction 21 corresponds to approximately 20 mm of coverage (at isocenter), leading to a total z-coverage of 8×20=160 mm in the illustration of FIG. 6. (As known in the art, coverage is often measured and specified as coverage at isocenter, i.e., center of rotation 24 as illustrated in FIG. 2).

According to the illustrated embodiment, second array of pixels 114 includes packs 124 having a pixel size of approximately 1 mm×1 mm. Each rectangular block 126 of second array of pixels 114 includes 16 channels along x-direction 23, and 32 slices along z-direction 21, for a total coverage of approximately 16 mm in x-direction 23 and approximately 32 mm in z-direction 21. As such, each rectangular block 126 of pixels provides approximately 16 mm of coverage along x-direction 23, and the eight blocks provide approximately 256 mm of coverage along z-direction 21, corresponding to approximately 160 mm of coverage along z-direction 21 at isocenter. Thus, in this embodiment, approximately 160 mm of coverage along z-direction 21 is provided in the illustrated 256 pixels. Further according to this embodiment, first array of pixels 110 includes packs 128 pixels having a resolution that is lower than the pixels of second array of pixels 114. As discussed, boundaries 118 correspond generally to defining coverage in detector assembly 18 between first FOV 120 and second FOV 122. As such, detector assembly 18 provides imaging data of an object over first FOV 120, and at a resolution that is different from (higher in this embodiment) imaging data obtained over second FOV 122.

Further and as illustrated in FIG. 6, first array of pixels 110 may include some detector packs that provide an increased resolution therein. Thus, according to this embodiment, two central packs 130 are illustrated that are centered along z-direction 21, having a resolution comparable to that provided by detector modules 20 provided in second array of pixels 114. This embodiment thus includes four corner sets of packs 132 having a lower resolution than second array of pixels 114 and of packs in first array of pixels 110 and within two central packs 130.

Accordingly, detector array 18 may be used in at least two modes of operation that correspond to:

1) a first mode using detectors 20 in second array of pixels 114 for high resolution provided over a full z-coverage 134, and using detectors 20 in first array of pixels 110 for low resolution (in order to reduce truncation and other errors that may result from a limited FOV over first FOV 120); and 2) a second mode using detectors 20 in first and second arrays of pixels 110, 114 but over a more limited z-coverage provided by two central packs 130. In this mode, limited x-rays in z-direction 21 may be provided by collimating, along z, using pre-patient collimator 27.

Further, referring back to FIG. 5, although not illustrated, the two modes of operation referred to may be accomplished using two corresponding bowtie filters—a first bowtie filter that corresponds to first mode of operation and having first and second x-ray filtration regions 102, 104 that correspond generally to first and second arrays of pixels 110, 114, and a second bowtie filter (not illustrated) having an enlarged second x-ray filtration region 104 that corresponds generally to first array of pixels 110 and provides full coverage of second FOV 122.

As illustrated with respect to FIG. 4, pack 51 includes 16 pixels along x-direction 23. As further discussed with respect to FIG. 6, eight packs 124 are shown in a module having 32 pixels each along z-direction 21. FIG. 6 also includes four corner sets of packs 132 having a lower resolution than those in the other portions of detector array 18. In one embodiment, referring to FIG. 7, each pack of the four corner sets of packs 132 is illustrated in an end view of a detector module 200 having four pixels 202 of a scintillator positioned on a backlit photodiode 204 and shown along x-direction 23. Each scintillator pixel 202 is separated and covered by a reflector 206 that may be, for instance, a material that includes TiO2, in order to reduce or eliminate crosstalk between pixels. Backlit photodiode 204 includes delineations of pixels with active regions 208. That is, as known in the art, active regions 208 of backlit photodiode 204 may be positioned in conjunction with scintillator pixels 202 such that photons generated in each scintillator pixel 202 are read in a separate and respective area 208 of backlit photodiode 204.

Figure 7:
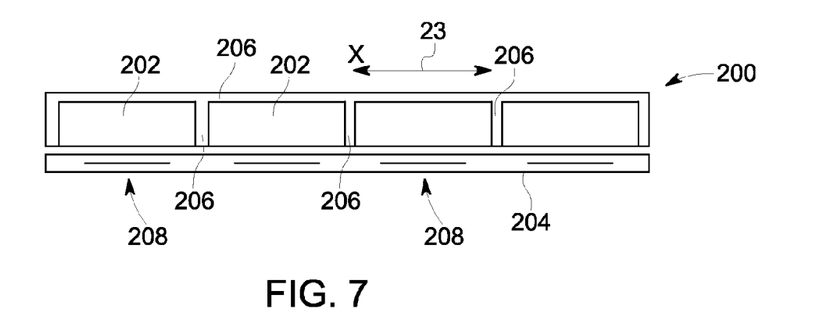
FIG. 7 illustrates an end view of a low-resolution detector module according to an embodiment of the invention.

Thus, according to this embodiment, pixels 202 are generally square (approximately 4 mm×4 mm in this embodiment, but may be 2 mm×2 mm, for instance, in other embodiments), having four pixels 202 illustrated in end view 200 and eight along z-direction 21 (in and out of the page, not shown), for a relatively low resolution 4×8 array. This compares to modules having a high-resolution 16×32 pack, such as packs 124 in second array of pixels 114, and in two central packs 130 extended over second FOV 122. In other words, referring to FIG. 6, second array of pixels 114 and arrays 136 include packs having high resolution 16×32 sets of pixels, and first array of pixels 110 includes packs having low resolution 4×8 sets of pixels (or other settings). As such, both modes of operation described above may be accomplished using detector array 18 illustrated in FIG. 6, using the low resolution detector modules 200 as illustrated in FIG. 7, in four corner sets of modules 132, which provides desired functionality at significant cost savings due to the use of low resolution packs. That is, because pixels 202 are larger, imaging data obtained therefrom is less sensitive to fabrication tolerances, scintillator homogeneity, and the like. Thus, modules fabricated having a lower resolution pixel can be fabricated with a significant reduction in overall cost. For instance, a higher pack yield can be expected for larger cell sizes, and less cell dicing is required. Further, a lower cost diode may be used (having fewer cell delineations), and fewer interconnections are required, leading to fewer ASICs, fewer interconnects, and flex circuits having fewer and lower density electrical runs or interconnects therein. As such, an overall higher module fabrication yield can be expected, as well.

Figure 8:
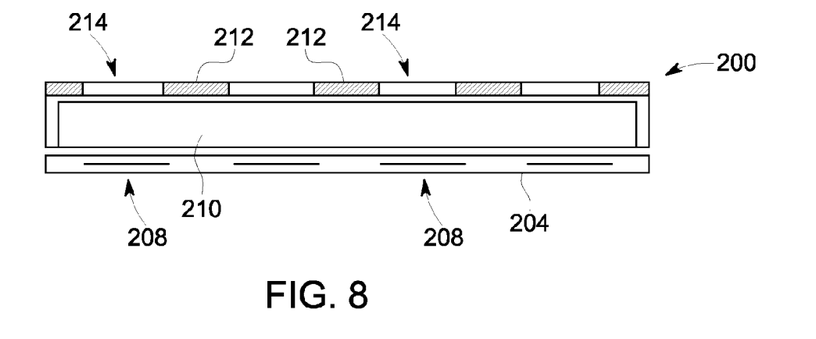
FIGS. 8-11 illustrate alternate low-resolution detector modules according to embodiments of the invention.

Low resolution modules for four corner sets of modules 132 may be fabricated according to other embodiments, according to the invention. FIGS. 8-11 illustrate additional and alternative embodiments for fabricating low-resolution modules that may be used in lieu of detector module 200 shown in FIG. 7. FIG. 8 illustrates an end view of module 200 having, in lieu of pixels 202 having individual scintillators, a single (undiced) scintillator 210 positioned on backlit photodiode 204. Instead of having separate scintillator pixels as illustrated in FIG. 7, pixels are delineated using an x-ray blocking material 212, such as an etched metal grid of, for instance, tungsten, having apertures 214 therein that correspond with active regions 208 of backlit photodiode 204. Further, because the resolution for four corner sets of modules 132 is lower, requirements for quantum detection efficiency (QDE) are relaxed as well. For instance, it may be desired to have a high-resolution scintillator having perhaps 98% QDE, while in a low resolution module only 85% QDE may be desired. Thus, because of the lower QDE, it is possible to use a thinner scintillator and a less expensive scintillator.

Figure 9:
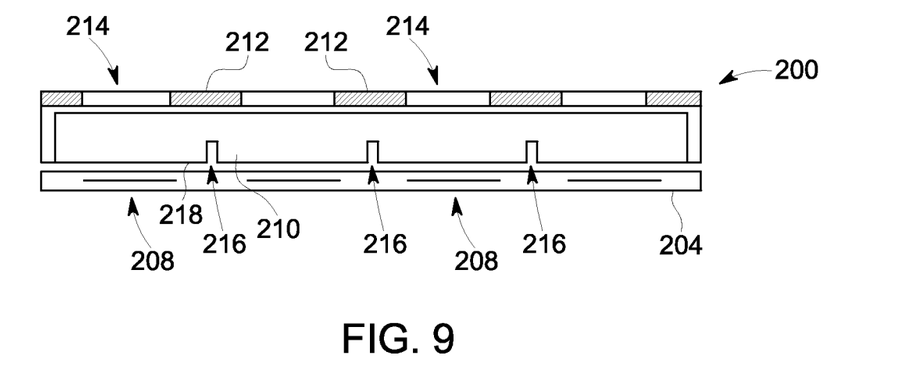

According to another embodiment, FIG. 9 illustrates module 200 having a single scintillator 210 and x-ray blocking material 212 with apertures 214 therein that correspond to active regions 208 of backlit photodiode 204, as with FIG. 8. In order to reduce cross-talk between pixels, notches 216 are included to further delineate pixels therein. And, although notches 216 are only illustrated in the end view along a y-z plane as understood in the art, it is to be understood that corresponding notches are also positioned in the x-y plane as well, in order to delineate pixels within scintillator 210. In fact such is the case with all embodiments where an end-view is illustrated and that pixels are delineated, as understood in the art, along the x-y plane as well. According to this embodiment, notches 216 are in a face 218 of scintillator, between single scintillator 210 and backlit photodiode 204, and may be to any depth that may reduce crosstalk. Notches 216 are positioned to correspond to x-ray blocking material 212 and between apertures 214. In a single scintillator 210 having for instance a thickness of 4 mm, notches 216 may have a depth of 1-3 mm, leaving enough integrity in single scintillator 210 for handling during fabrication, while providing a reduction in crosstalk. According to one embodiment, notches 216 may be filled with a reflector, such as reflector 206 as discussed above.

Figure 10:
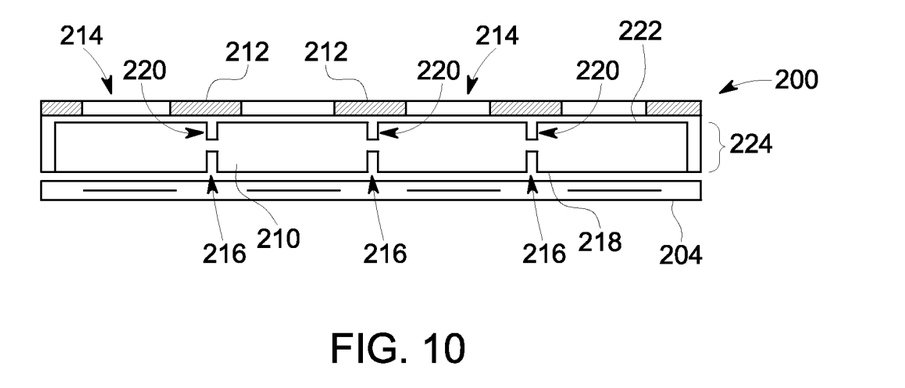

According to yet another embodiment, FIG. 10 illustrates module 200 having single scintillator 210, and pixel delineations using x-ray blocking material 212 with apertures 214. Per the embodiment of FIG. 9, module 200 includes notches 216 in face 218. However, to further reduce crosstalk, a second set of notches 220 may be positioned in a second face 222 of single scintillator 210. In the embodiment illustrated in FIG. 10, notches 216, 220 are coincident or collinear with one another. That is, notches 216, 220 are positioned proximate one another such that overall crosstalk is reduced. As such, because notches 216, 220 are coincident, it is evident that the sum of their depths cannot exceed a total thickness 224 of single scintillator 210.

Figure 11:
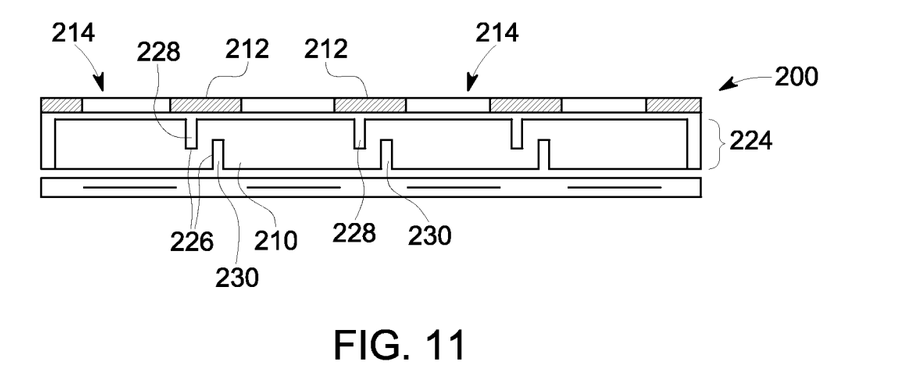

According to still another embodiment, FIG. 11 illustrates module 200 having single scintillator 210, and pixel delineations using x-ray blocking material 212 with apertures 214. In order to reduce crosstalk, module 200 includes two offset notches 226 positioned proximate x-ray blocking material 212 and positioned between apertures 214. According to this embodiment, two offset notches 226 each include a first notch 228 and a second notch 230. Because notches 226 are offset from one another, the sum of their depths may be greater than total thickness 224 of single scintillator 210. Thus, first notches 228 may each be a depth that is greater than half of total thickness 224, and second notches 230 may likewise be a depth that is also greater than half of total thickness 224. As such, a total thickness of each set of offset notches 226 may exceed total thickness 224 of single scintillator 210, and a total crosstalk between pixels is thereby reduced.

It is contemplated that resolution of the embodiments of module 200, illustrated in FIGS. 7-11, may be greater or less than that illustrated. That is, in the illustrated embodiments, four pixels or pixel delineations are shown along a channel direction, and correspondingly 8 pixels or pixel delineations are included in a slice or z-direction (in and out of the page of the respective illustrations). However, the invention is not to be so limited and greater sizes of pixels may be included, such as packs having 2×4, or 3×6, as examples. Smaller pixel sizes may be included as well, such as packs having 5×10 or 6×12. However, as recognized, a pixel array size of 8×16 would correspond to the array size described with respect to FIG. 4 above. Thus, it is to be recognized that, according to the invention, any pixel array size may be designated as a 'high-resolution' pixel size for detector array 18, and any pixel array size may be designated as a 'low-resolution' pixel size (for four corner sets of modules 132 of detector array 18, for example), and that such a designation is relative, providing improvements and cost savings according to the invention by placing low resolution detectors as four corner sets of packs 132. Further, it is to be understood that the relative pixel array sizes may be selected not only on cost, but also on for instance a tradeoff between crosstalk and quantum detection efficiency (QDE), as one example and as understood in the art.

Figure 12:
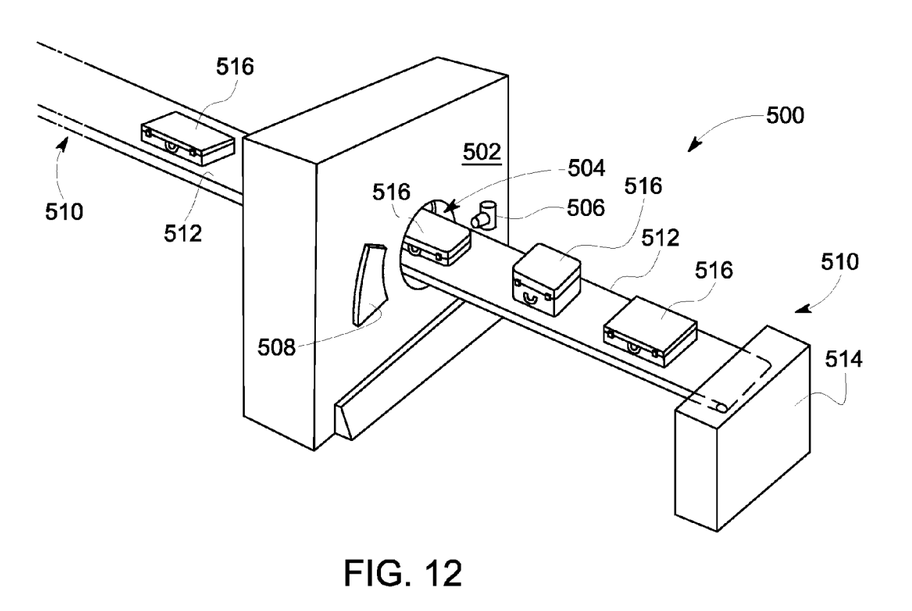
FIG. 12 is a pictorial view of a CT system for use with a non-invasive package inspection system.

Referring now to FIG. 12, package/baggage inspection system 500 includes a rotatable gantry 502 having an opening 504 therein through which packages or pieces of baggage may pass. The rotatable gantry 502 houses a high frequency electromagnetic energy source 506 as well as a detector assembly 508 having scintillator arrays comprised of scintillator cells similar to that shown in FIGS. 1 and 2. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

A technical contribution for the disclosed method and apparatus is that it provides for a computer implemented method and apparatus of low resolution imaging in an imaging application.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

According to an embodiment of the invention, a CT system includes a rotatable gantry having an opening to receive an object to be scanned, an x-ray source configured to project an x-ray beam toward the object, and a detector array configured to detect x-rays passing through the object. The detector array includes a first array of pixels positioned to receive x-rays that pass to the detector array outside a first field-of-view (FOV) to a second FOV, the first array of pixels providing a first resolution, and a second array of pixels positioned to receive x-rays passing through the first FOV, the second array of pixels providing a second resolution that is different from the first resolution. The system includes a data acquisition system (DAS) configured to receive outputs from the detector array, and a computer programmed to acquire projections of imaging data of the object, and generate an image of the object using the imaging data.

According to another embodiment of the invention, a method of fabricating a detector assembly includes positioning a first detector array, having detector modules comprising a first resolution, to receive imaging data over a second field-of-view (FOV) and outside a first FOV, and positioning a second detector array, having detector modules comprising a second resolution, to receive imaging data over the first FOV, wherein the second resolution is different from the first resolution.

According to another embodiment of the invention, a non-transitory computer readable storage medium having stored thereon a computer program comprising instruction which, when executed by a computer, cause the computer to obtain first imaging data from a first plurality of detector modules, having a first resolution, that are positioned to receive the first imaging data over a second field-of-view (FOV) that is outside of a first FOV, obtain second imaging data from a second plurality of detector modules, having a second resolution, that are positioned to receive the second imaging data over the first FOV, wherein the second resolution is greater than the first resolution, and reconstruct an image using the imaging data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A CT system comprising:
a rotatable gantry having an opening to receive an object to be scanned;
an x-ray source configured to project an x-ray beam toward the object;
a detector array configured to detect x-rays passing through the object, the detector array comprising:
a first array of pixels positioned to receive x-rays that pass to the detector array outside a first field-of-view (FOV) to a second FOV, the first array of pixels providing a first resolution; and
a second array of pixels positioned to receive x-rays passing through the first FOV, the second array of pixels providing a second resolution that is different from the first resolution;
a data acquisition system (DAS) connected to the detector array and configured to receive outputs from the detector array; and
a computer programmed to:
acquire projections of imaging data of the object from the DAS; and
generate an image of the object using the imaging data;
wherein the first array of pixels is comprised of detector modules having a first scintillator coupled to a first photodiode, wherein the first scintillator comprises a first cross-sectional area that is essentially orthogonal to x-rays of the x-ray beam passing thereto from the x-ray source;
wherein several pixels of the first array of pixels are comprised of a single scintillator, wherein the detector array includes an x-ray blocking material coupled to a first surface of the single scintillator, the x-ray blocking material having a plurality of rungs forming a plurality of openings therein that delineate the first array of pixels, wherein the rungs are positioned to block x-rays passing from the x-ray source to the single scintillator; and
wherein the single scintillator includes a first plurality of notches positioned therein and in a second surface of the single scintillator that is opposite the first surface, wherein each notch of the first plurality of notches corresponds to a respective rung position of the plurality of rungs, wherein a first notch of the first plurality of notches is notched to a first depth, and wherein the notches are pixels in both an x-direction and a z-direction and are orthogonal to each other.

2. The CT system of claim 1 wherein the second resolution is higher than the first resolution.

3. The CT system of claim 2 wherein the first array of pixels includes a third array of pixels that extend through the entire second FOV, wherein:
the third array of pixels provides a detector resolution that corresponds with the second resolution; and
the third array of pixels provide an amount of z-coverage that is less than a total z-coverage of the detector array.

4. The CT system of claim 1 wherein the second array of pixels includes an isochannel of the detector array.

5. The CT system of claim 1 wherein the second array of pixels comprises detector modules having a second scintillator coupled to a first photodiode, wherein:
the second scintillator comprises a second cross-sectional area that is essentially orthogonal to x-rays of the x-ray beam passing thereto from the x-ray source; and
the first cross-sectional area of the first scintillator is larger than the second cross-sectional area of the second scintillator.

6. The CT system of claim 1 wherein the single scintillator includes a second plurality of notches positioned therein, each or which corresponds to a respective rung position of the plurality of rungs, and each of which is in the first surface of the single scintillator, wherein a second notch of the second plurality of notches is notched to a second depth.

7. The CT system of claim 6 wherein:
the first depth and second depth sum to a value that is less than a thickness of the single scintillator;
the first notch and the second notch are arranged collinearly such that x-rays passing through the first notch from the x-ray source also pass through the second notch; and
notches are positioned in both an x-direction and a z-direction and are orthogonal to each other in order to delineate pixels in the single scintillator.

8. The CT system of claim 6 wherein:
the first depth and second depth sum to a value that is greater than a thickness of the single scintillator;
the first notch and the second notch are offset from one another such that primary x-rays that pass through the first notch do not pass through the second notch; and
notches are provided in both an x-direction and a z-direction and are orthogonal to each other in order to delineate pixels in the single scintillator.

9. A method of fabricating a detector assembly comprising:
positioning a first detector array, having detector modules comprising a first resolution, to receive imaging data over a second field-of-view (FOV) and outside a first FOV; and
positioning a second detector array, having detector modules comprising a second resolution, to receive imaging data over the first FOV, wherein the second resolution is different from the first resolution;
wherein a scintillator of a detector module of the first detector array is larger than a scintillator of a detector module of the second detector array;
wherein the scintillator of the detector module of the first detector array is a single scintillator that encompasses a plurality of pixels of the detector of the first detector array, with the first detector array including an x-ray blocking material coupled to a first surface of the single scintillator, the x-ray blocking material having a plurality of rungs forming a plurality of openings therein that delineate the pixels, wherein the rungs are positioned to block x-rays passing from the x-ray source to the single scintillator; and
wherein the single scintillator includes a first plurality of notches positioned therein and in a second surface of the single scintillator that is opposite the first surface, wherein each notch of the first plurality of notches corresponds to a respective rung position of the plurality of rungs, wherein a first notch of the first plurality of notches is notched to a first depth, and wherein the notches are pixels in both an x-direction and a z-direction and are orthogonal to each other.

10. The method of claim 9 comprising positioning a third detector array, having detector modules comprising the first resolution, to receive imaging data over the second FOV and outside the first FOV, but positioned to receive the imaging data at a detector position that is asymmetrically located with respect to an isochannel and the first detector array.

11. The method of claim 10 wherein the detector positions are asymmetrically located with respect to a plane of rotation of the first and second detector arrays.

12. The method of claim 9 wherein the second resolution is higher than the first resolution.

13. The method of claim 9 comprising positioning detector modules having the second resolution within the first detector array to receive imaging data at the first resolution over the entire second FOV.

14. The method of claim 3 wherein:
   the detector modules having the second resolution that are positioned within the first detector array, are positioned to provide a z-coverage that is less than a total z-coverage of the first detector array.

* * * * *

UNITED STATES PATENT AND TRADEMARK OFFICE
CERTIFICATE OF CORRECTION

PATENT NO.        : 8,761,333 B2
APPLICATION NO.   : 13/208445
DATED             : June 24, 2014
INVENTOR(S)       : Ikhlef et al.

It is certified that error appears in the above-identified patent and that said Letters Patent is hereby corrected as shown below:

In the Claims

Col. 13, line 14 (Claim 14), delete "The method of claim 3 wherein:" and substitute therefore -- The method of claim 13 wherein: --.

Signed and Sealed this
Seventh Day of October, 2014

Michelle K. Lee
*Deputy Director of the United States Patent and Trademark Office*